United States Patent
Furnish et al.

(10) Patent No.: US 11,207,512 B2
(45) Date of Patent: Dec. 28, 2021

(54) AUTOMATIC MEDICAL VALVE WITH A VARIABLE DIAMETER SEAL

(71) Applicant: Freudenberg Medical, LLC, Carpinteria, CA (US)

(72) Inventors: Greg Furnish, Louisville, KY (US); Anthony Appling, Crestwood, KY (US); Ben Morris, Jeffersonville, IN (US); Timothy S. Zeis, Charlestown, IN (US)

(73) Assignee: FREUDENBERG MEDICAL, LLC, Carpinteria, CA (US)

( * ) Notice: Subject to any disclaimer, the term of this patent is extended or adjusted under 35 U.S.C. 154(b) by 1026 days.

(21) Appl. No.: 15/865,935

(22) Filed: Jan. 9, 2018

(65) Prior Publication Data

US 2018/0126144 A1      May 10, 2018

Related U.S. Application Data

(63) Continuation-in-part of application No. 14/726,099, filed on May 29, 2015, now Pat. No. 9,884,175.
(Continued)

(51) Int. Cl.
*A61M 39/06*        (2006.01)

(52) U.S. Cl.
CPC ... *A61M 39/0613* (2013.01); *A61M 2039/068* (2013.01); *A61M 2039/0673* (2013.01); *A61M 2205/0216* (2013.01)

(58) Field of Classification Search
CPC ............ A61M 39/06; A61M 2039/062; A61M 2039/0626; A61M 2039/0673;
(Continued)

(56) References Cited

U.S. PATENT DOCUMENTS

| 4,921,479 A | 5/1990 | Grayzel |
| 5,195,980 A | 3/1993 | Catlin |

(Continued)

FOREIGN PATENT DOCUMENTS

| EP | 2965685 A1 | 1/2016 |
| WO | 2005058409 A1 | 6/2005 |

(Continued)

*Primary Examiner* — Jason E Flick
(74) *Attorney, Agent, or Firm* — Dickinson Wright PLLC

(57) ABSTRACT

A medical valve assembly includes a tube extending between proximal and distal tube ends. A plunger plate extends radially from the distal tube end, and a valve housing surrounds the tube and extends between proximal and distal valve housing ends. The valve housing includes a flange extending radially inwardly from the distal valve housing end and disposed in spaced relationship with the plunger plate to define a distance dimension D extending therebetween. An elastomeric seal is compressed between the plunger plate and the flange to establish a closed condition of the medical valve assembly. The elastomeric seal axially moves one of the valve housing and the tube relative to the other when a medical device is inserted into the medical valve assembly to automatically increase the distance dimension and establish an open and sealed condition of the medical valve assembly with the inserted medical valve.

16 Claims, 10 Drawing Sheets

Related U.S. Application Data

(60) Provisional application No. 62/151,835, filed on Apr. 23, 2015.

(58) Field of Classification Search
CPC .... A61M 2039/068; A61M 2205/0216; A61M 39/0613; A61B 17/3498
See application file for complete search history.

(56) References Cited

U.S. PATENT DOCUMENTS

| | | | |
|---|---|---|---|
| 5,256,150 | A | 10/1993 | Quiachon et al. |
| 5,338,313 | A | 8/1994 | Mollenauer et al. |
| 5,484,418 | A | 1/1996 | Quiachon et al. |
| 5,591,137 | A | 1/1997 | Stevens |
| 5,895,376 | A | 4/1999 | Schwartz et al. |
| 5,935,112 | A | 8/1999 | Stevens et al. |
| 5,935,122 | A | 8/1999 | Fourkas et al. |
| 5,967,490 | A | 10/1999 | Pike |
| 5,997,508 | A | 12/1999 | Lunn et al. |
| 6,183,443 | B1 | 2/2001 | Kratoska et al. |
| 6,443,979 | B1 | 9/2002 | Stalker et al. |
| 6,572,590 | B1 * | 6/2003 | Stevens ............ A61M 39/0613 604/246 |
| 7,967,790 | B2 | 6/2011 | Whiting et al. |
| 8,025,641 | B2 | 9/2011 | Bettuchi |
| 8,083,728 | B2 | 12/2011 | Rome |
| 2004/0178586 | A1 | 9/2004 | Junge |
| 2005/0085789 | A1 | 4/2005 | Khan et al. |
| 2005/0085841 | A1 | 4/2005 | Eversull et al. |
| 2005/0261664 | A1 | 11/2005 | Rome et al. |
| 2006/0241671 | A1 | 10/2006 | Greenhalgh |
| 2007/0225647 | A1 | 9/2007 | Luther et al. |
| 2007/0260195 | A1 | 11/2007 | Bartholomew et al. |
| 2010/0094392 | A1 | 4/2010 | Nguyen et al. |
| 2011/0319859 | A1 | 12/2011 | Zeytoonian et al. |
| 2012/0238958 | A1 | 9/2012 | Moore |
| 2012/0310166 | A1 | 12/2012 | Huff |
| 2013/0006195 | A1 | 1/2013 | Sonderegger et al. |
| 2015/0025477 | A1 | 1/2015 | Evans |
| 2015/0038919 | A1 | 2/2015 | Bramwell et al. |
| 2016/0038701 | A1 | 2/2016 | White et al. |
| 2016/0089492 | A1 | 3/2016 | Burnard et al. |
| 2016/0158435 | A1 | 6/2016 | Wu et al. |
| 2016/0339891 | A1 | 11/2016 | Arumugham et al. |

FOREIGN PATENT DOCUMENTS

| | | |
|---|---|---|
| WO | 2013106447 A1 | 7/2013 |
| WO | 2013115221 A1 | 8/2013 |

* cited by examiner

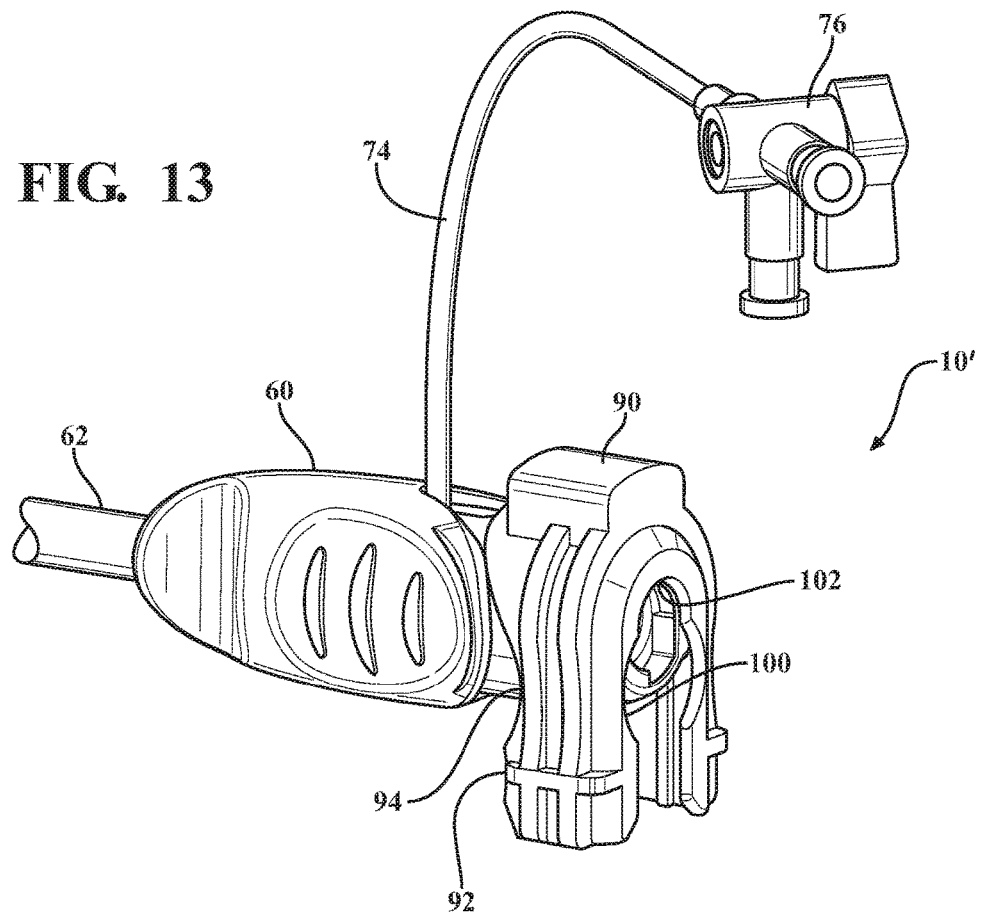
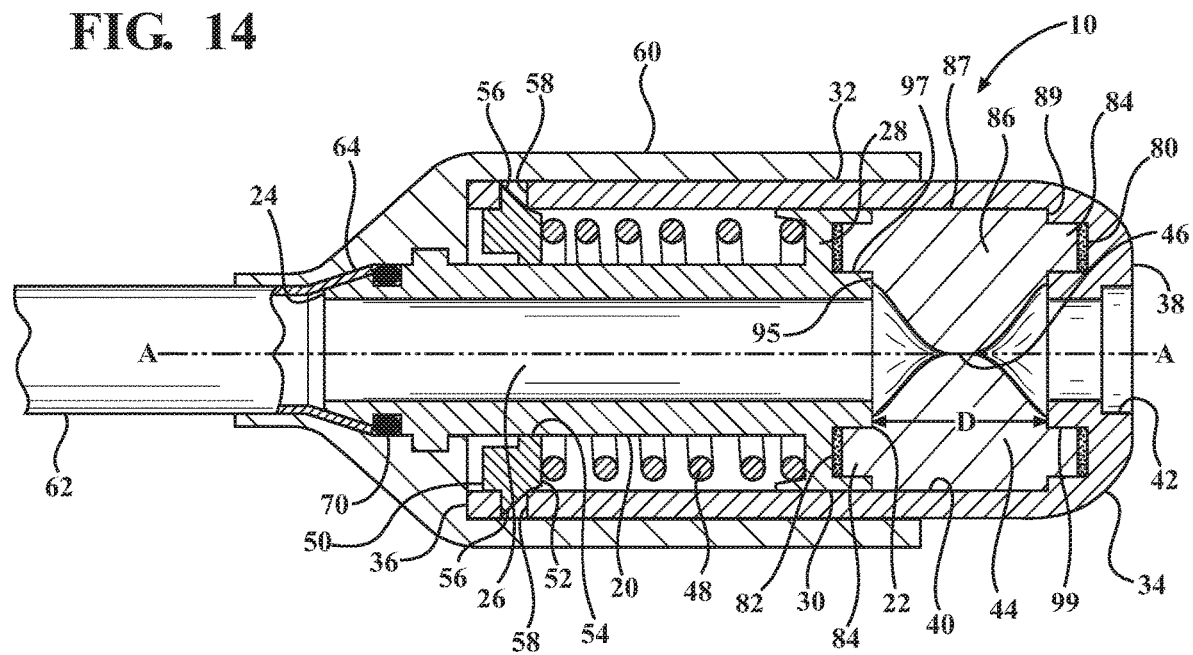

AUTOMATIC MEDICAL VALVE WITH A VARIABLE DIAMETER SEAL

RELATED APPLICATION

The subject application is a continuation-in-part of U.S. patent application Ser. No. 14/726,099 filed on May 29, 2015, which claims priority to U.S. Provisional Application Ser. No. 62/151,835 filed on Apr. 23, 2015, the entire disclosures of which are incorporated herein by reference.

BACKGROUND OF THE INVENTION

1. Field of the Invention

The present disclosure relates generally to medical devices and procedures. In particular, the present disclosure relates to hemostatic valves and systems, and methods of using the same.

2. Description of the Prior Art

This section provides background information related to the present disclosure which is not necessarily prior art.

Numerous procedures have been developed that involve the percutaneous insertion of a medical device into a body vessel of a patient, with the medical device being introduced into the vessel by a variety of known techniques. Each of these procedures must control the flow of bodily fluids when the medical device is inserted into the body vessel. Accordingly, medical valves, such as hemostatic valves, iris valves, laparoscopic ports, or the like, are often used to limit or prevent blood/fluid or $CO_2$/gas loss during the procedure.

Hemostatic valves often incorporate an elastomeric slit septum disk to control fluid flow through the medical device. However, disk valves are subject to deformation with both time and use, and often can tear or become dislodged during insertion and/or withdrawal of the medical device. Furthermore, disk valves are not designed to provide an effective seal across a wide range of differently sized medical devices. Although the disk valve can be modified to accommodate these situations, such as with increased tensile and/or elongation properties, this modification leads to increased resistance, and thus require the use of excessive force when the medical device is inserted and withdrawn through the disk valve.

Iris valves can include an elastomeric sleeve that is disposed within a valve body and which is interconnected to a rotatable cap. When the cap is rotated in a first direction, an opening extending through the elastomeric sleeve is opened. Conversely, when the cap is rotated in a second opposite direction, the elastomeric sleeve is twisted and constricted to effectuate a closure of the elastomeric sleeve. However, if the operator stops the rotation, the elastomeric sleeve can revert, or recoil, back to the open position. Additionally, even when the elastomeric sleeve is held in the closed position, gaps or channels extend therethrough as a result of the twisting or enfolding required to effectuate a closure. Accordingly, fluid can leak through the iris valve in the closed position. Further, the continuous twisting and constricting of the elastomeric sleeve leads to wear of the sleeve, such as through tearing.

The drawbacks associated with the existing medical valves are further exemplified when one considers that a single medical valve often is used to insert multiple medical devices during a single procedure. For example, a hemostatic valve may be used first for introducing a delivery catheter, followed by an interventional catheter. In this example, the hemostatic valve must be able to provide a hemostatic seal under a variety of conditions, i.e., accommodate a variety of different sized medical devices. Additionally, the hemostatic valve device must be able to quickly adjust to use of each of these different medical devices, otherwise significant fluid loss can occur through the medical valve.

SUMMARY OF THE INVENTION

This section provides a general summary of the disclosure and is not intended to be a comprehensive disclosure of its full scope, aspects, objectives, and/or all of its features.

A medical valve assembly for use in inserting a medical device into a body vessel of a patient includes a tube extending between a proximal tube end and a distal tube end to define a passageway extending longitudinally along an axis between the tube ends. A plunger plate extends radially from the proximal tube end and a valve housing surrounds the tube about the proximal tube end. The valve housing extends from a proximal valve housing end to a distal valve housing end and includes a flange extending radially inwardly from the distal valve housing end, with the flange disposed in spaced relationship with respect to the plunger plate so as to define a distance dimension therebetween. An elastomeric seal is compressed between the plunger plate and the flange and has an inner diameter for use in establishing a variable seal of the medical valve assembly. The elastomeric seal is configured to automatically move one of the valve housing and the tube axially relative to the other when a medical device is inserted into the medical valve assembly. This axial movement varies the distance dimension between the plunger plate and the flange to allow the inner diameter of the elastomeric seal to variably adjust for sealing the medical valve assembly to the inserted medical device. Put another way, axial movement of one of the valve housing or the tube relative to the other in response to insertion of the medical device automatically varies a compression load on the elastomeric seal and allows the inner diameter of the elastomeric seal to be concurrently varied or adjusted in size. As a result, the size of the inner diameter of the elastomeric seal is able to quickly and automatically be adjusted to the size of the medical device by simply inserting the medical device into the medical valve assembly. This allows the medical valve assembly to be used with a variety of differently sized medical devices, even during the same procedure.

The elastomeric seal defines an annular void extending radially inwardly from an outer wall towards the inner diameter to decrease a requisite compression force for effectuating a reduction of the inner diameter of the elastomeric seal and a closed condition of the medical valve assembly. This advantageously allows the elastomeric seal to be comprised of an elastomeric material having a higher or increased durometer value which ultimately improves the durability of the elastomeric seal.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments, and are not all possible implementations and thus are not intended to limit the scope of the present disclosure.

FIG. 13 is a perspective view of the second embodiment of the medical valve assembly illustrating the clip disposed in a third position;

FIG. 14 is a cross-sectional view of the second embodiment of the medical valve assembly in a closed condition and illustrated without the clip;

DESCRIPTION OF THE ENABLING EMBODIMENTS

Example embodiments will now be described more fully with reference to the accompanying drawings. The example embodiments are provided so that this disclosure will be thorough and fully convey the scope to those skilled in the art. Numerous specific details are set forth such as examples of specific components, devices, mechanisms, assemblies, and methods to provide a thorough understanding of various embodiments of the present disclosure. It will be apparent to those skilled in the art that specific details need not be employed, that example embodiments may be embodied in many different forms, and that neither should be construed to limit the scope of the disclosure. With this in mind, the present disclosure is generally directed to medical valve assemblies of the type used to introduce and withdrawal a medical device (i.e., a guide wire, catheter, stent, filter, etc.) into a body vessel of a patient. In particular, the medical valve assembly of the present disclosure incorporates an automatic variable seal arrangement for controlling an entry dimension of the variable seal arrangement.

Figure 1:
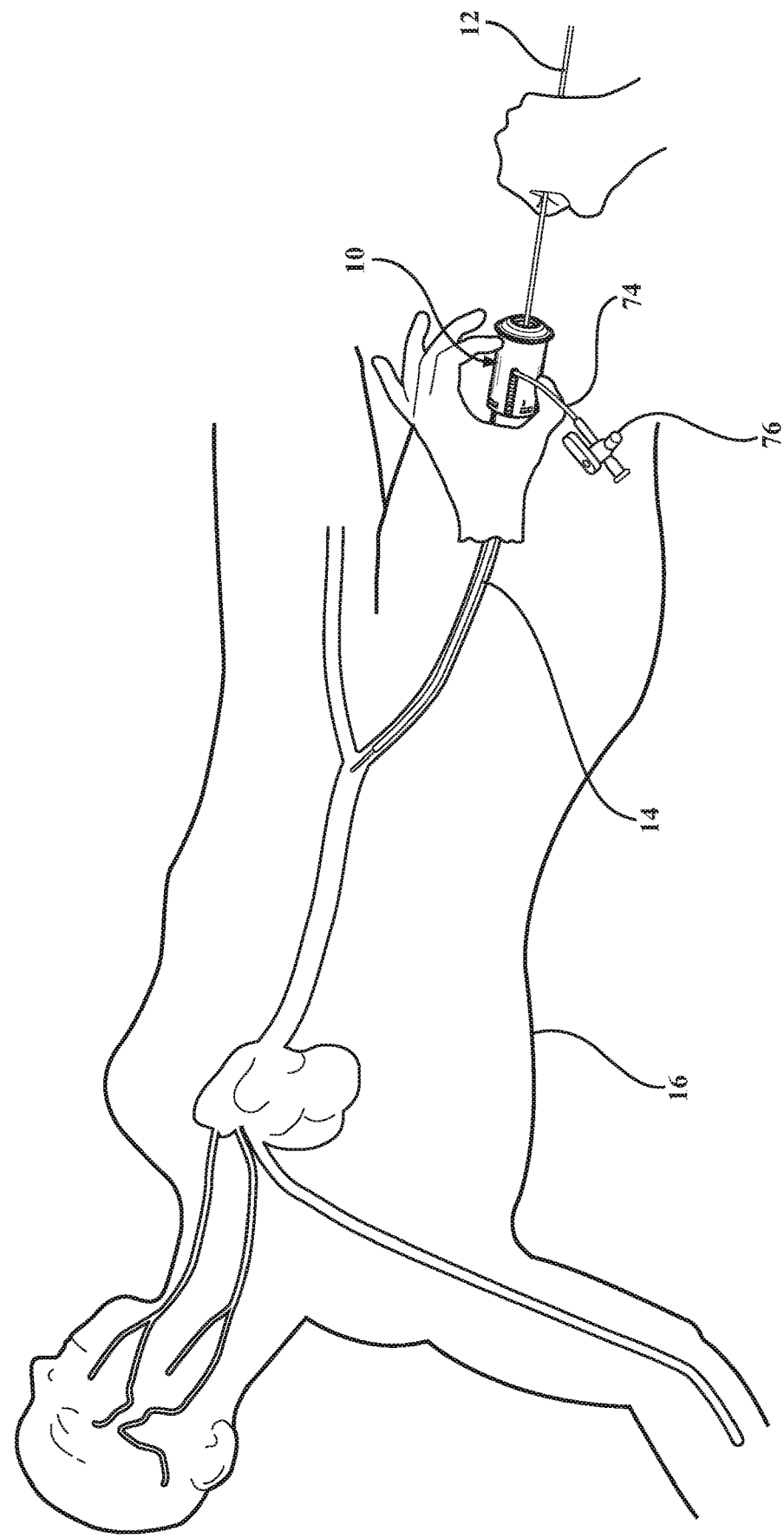
FIG. 1 is an environmental view of a first embodiment of the automatic medical valve assembly constructed in accordance with the principles of the present disclosure and illustrating a user interacting therewith.
Figure 9:
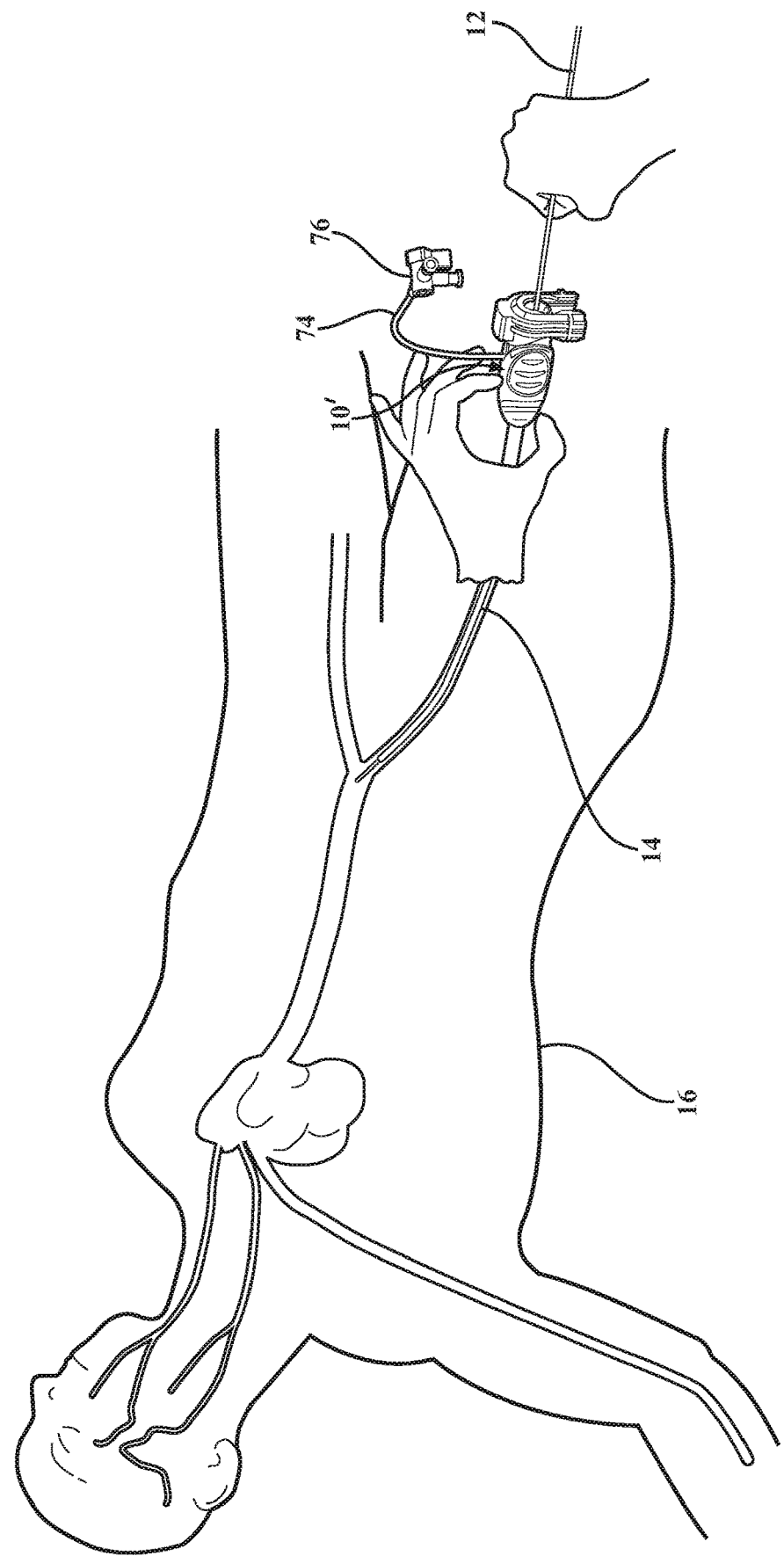
FIG. 9 is an environmental view of a second embodiment of the automatic medical valve assembly constructed in accordance with the principles of the present disclosure and illustrating a user interacting therewith.

Referring to the Figures, wherein like numerals indicate corresponding parts throughout the several views, an environmental view of a first embodiment of a medical valve assembly 10 and a second embodiment of a medical valve assembly 10' is generally shown in FIGS. 1 and 9, respectively. As illustrated therein, each medical valve assembly 10, 10' is of the type for use with a medical device 12, such as a guide wire, catheter, stent, filter, vessel occlusion device, or the like. As will be explained in more detail below, as the medical device 12 is inserted and guided through the medical valve assembly 10 and into a body vessel 14 of a patient 16, the medical valve assembly 10 will automatically effect a variable seal with the medical device 12.

As best shown in FIGS. 2, 4, 5, 10, 14, and 15 each medical valve assembly 10, 10' includes a tube 20 extending between a proximal tube end 22 and a distal tube end 24 to define a passageway 26 extending longitudinally along an axis A between the tube ends 22, 24, with the passageway 26 being sized to receive a variety of differently sized medical devices 12. A plunger plate 28 extends radially from the proximal tube end 22 to define an outer plunger plate surface 30 extending in spaced and parallel relationship to the axis A. A valve housing 32 is disposed in surrounding relationship with the tube 20 about the proximal tube end 22 and extends from a proximal valve housing end 34 to a distal valve housing end 36 to overlay the outer plunger plate surface 30. As best shown in FIGS. 4, 5, 14, and 15, the valve housing 32 is disposed in spaced and axial or parallel relationship with the tube 20 between the distal valve housing end 36 and the plunger plate 28.

The valve housing 32 includes a flange 38 extending radially inwardly from the proximal valve housing end 36. The flange 38 is disposed in circumferentially spaced relationship with the plunger plate 28 to define a distance dimension D, as well as a cavity 40, extending therebetween. The flange 38 also defines an opening 42 aligned on the axis A and that is sized to receive a variety of differently sized medical devices 12. An elastomeric seal 44 is installed in the cavity 40 and normally is pre-loaded or compressed between the plunger plate 28 and the flange 38 by a compression member 48 (or spring). As will be described in more detail below, the elastomeric seal 44 establishes an automatic variable seal of the medical valve assembly 10 for sealing the medical valve assembly 10 to a variety of differently sized medical devices 12. As best shown in FIGS. 2-4, and 14, the compression member 48 is disposed within the valve housing 32 and is compressed against the plunger plate 28 for effectuating a closing or decreasing of an inner diameter 46 of the elastomeric seal 44 to establish a closed condition of the medical valve assembly 10. Put another way, the compression member 48 is under a slight preload to maintain the elastomeric seal 44 in a compressed state that achieves apposition of the inner diameter 46 of the elastomeric seal 44, thus establishing the closed condition of the medical valve assembly 10. As best shown in FIGS. 4 and 14, in the closed condition of the medical valve assembly 10, the elastomeric seal 44 completely isolates or seals the opening 42 of the valve housing 32 from the passageway 26 of the tube 20. In an aspect, the compression member 48 comprises a coil spring radially disposed between the valve housing 32 and the tube 20 and compressed between the first valve housing end 34 and the plunger plate 28. However, any other suitable compression member, such as a leaf spring or the like, could be utilized without departing from the scope of the subject disclosure.

Figure 4:
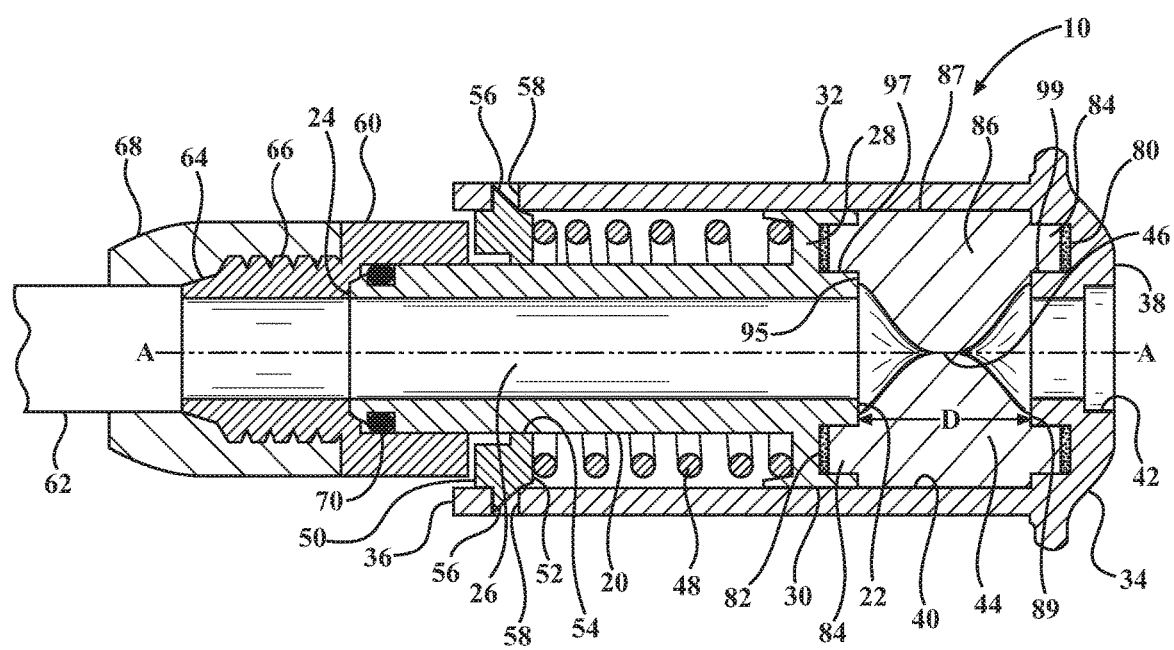
FIG. 4 is a cross-sectional view of the first embodiment of the medical valve assembly in a closed condition.
Figure 5:
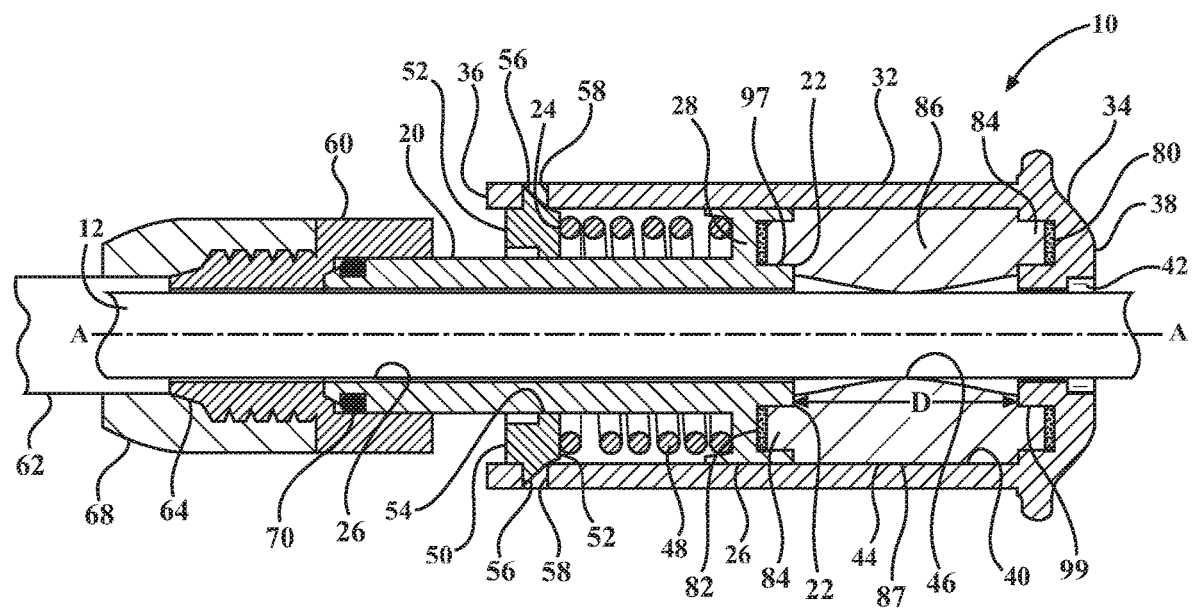
FIG. 5 is a cross-sectional view of the first embodiment of the medical valve assembly in an open condition.

With the elastomeric seal 44 in its closed position, the medical device 12 is positioned to be inserted serially through the opening 42, the inner diameter 46 of the elastomeric seal 44 and the passageway 26 of the medical valve assembly 10. When a medical device 12 is inserted through the opening 42 of the valve housing 32, the medical device 12 engages the elastomeric seal 44 with an insertion force that is transferred or exerted radially outward on the elastomeric seal 44, causing the elastomeric seal 44 to axially expand and counteract the biasing force of the compression member 48 with an axial force that is exerted on the plunger plate 28 and the flange 38 by the axially expanded elastomeric seal 44. Put another way, the insertion force of the medical device 12 is transferred through the elastomeric seal 44 to compress the compression member 48 and effectuate an axial movement of one of the valve housing 32 or the tube 20 relative to the other. The increased distance dimension D between the plunger plate 28 and the flange 38 changes the compression load exerted on the elastomeric seal 44 which, in turn, allows the inner diameter 46 of the elastomeric seal 44 to be expanded or increased in size to establish the open condition of the medical valve assembly 10. According to an aspect, the automatic adjustment of the inner diameter 46 of the elastomeric seal 44 increases proportionately with the distance dimension D. Thus, the medical valve 12 allows the user to automatically establish the open condition of the medical valve assembly 10 simply by inserting the medical device 12 into the medical valve assembly 10 and engaging the elastomeric seal 44. When the medical device 12 is removed from the medical valve assembly 10, the biasing force of the compression member 48 compresses the elastomeric seal 44 back to its original size to effectuate a reduction or decrease in the inner diameter 46 of the elastomeric seal 44 to re-establish the closed condition of the medical valve assembly 10. As best shown in FIGS. 4 and 5, when the valve housing 32 or the tube 20 is axially moved, the plunger plate 28 or the valve housing 32 axially slides relative to the other along the outer plunger plate surface 30. The outer plunger plate surface 30 guides a sliding axial movement between the valve housing 32 and the tube 20.

Figure 2:
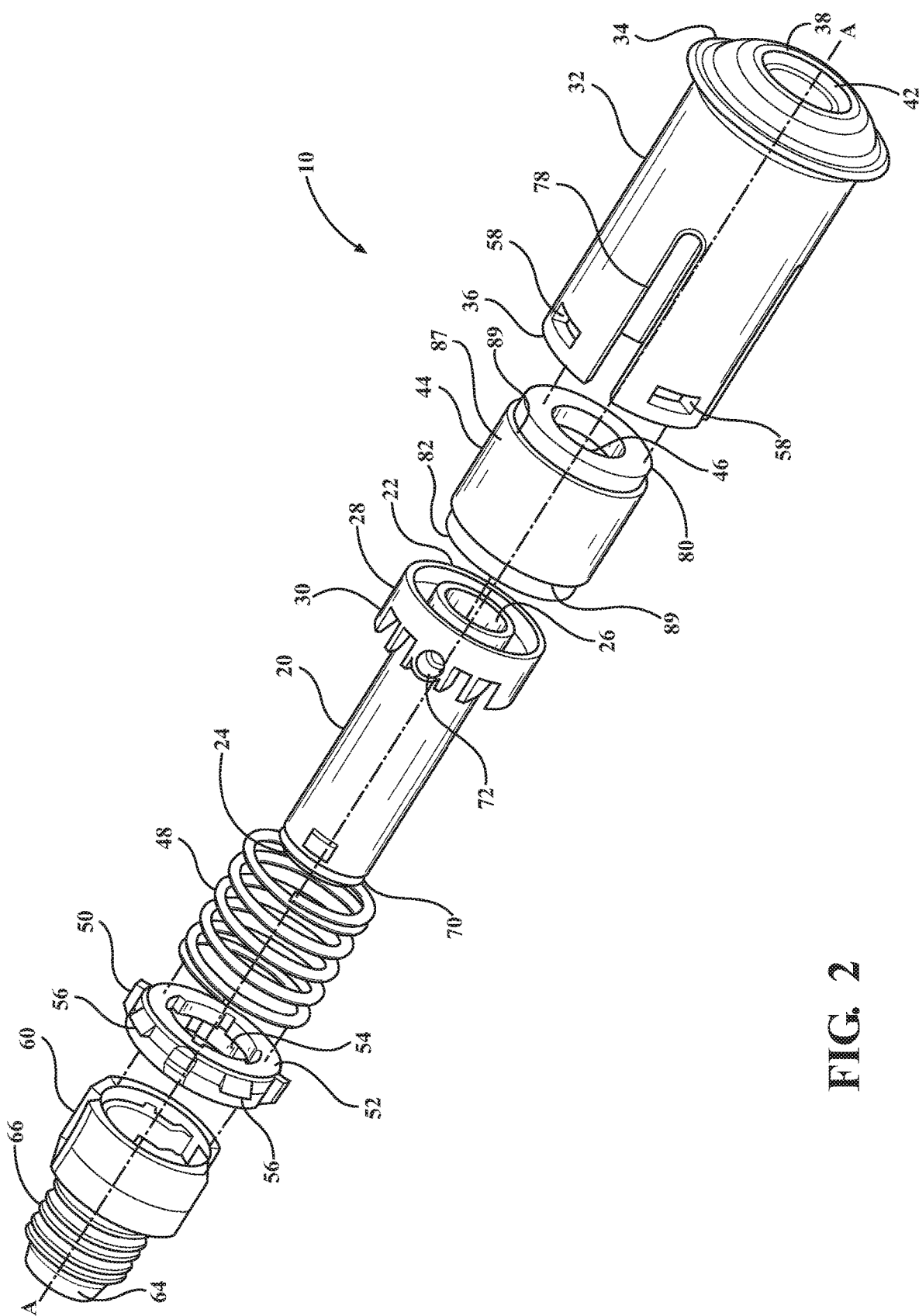
FIG. 2 is an exploded perspective view of the first embodiment of the medical valve assembly.
Figure 10:
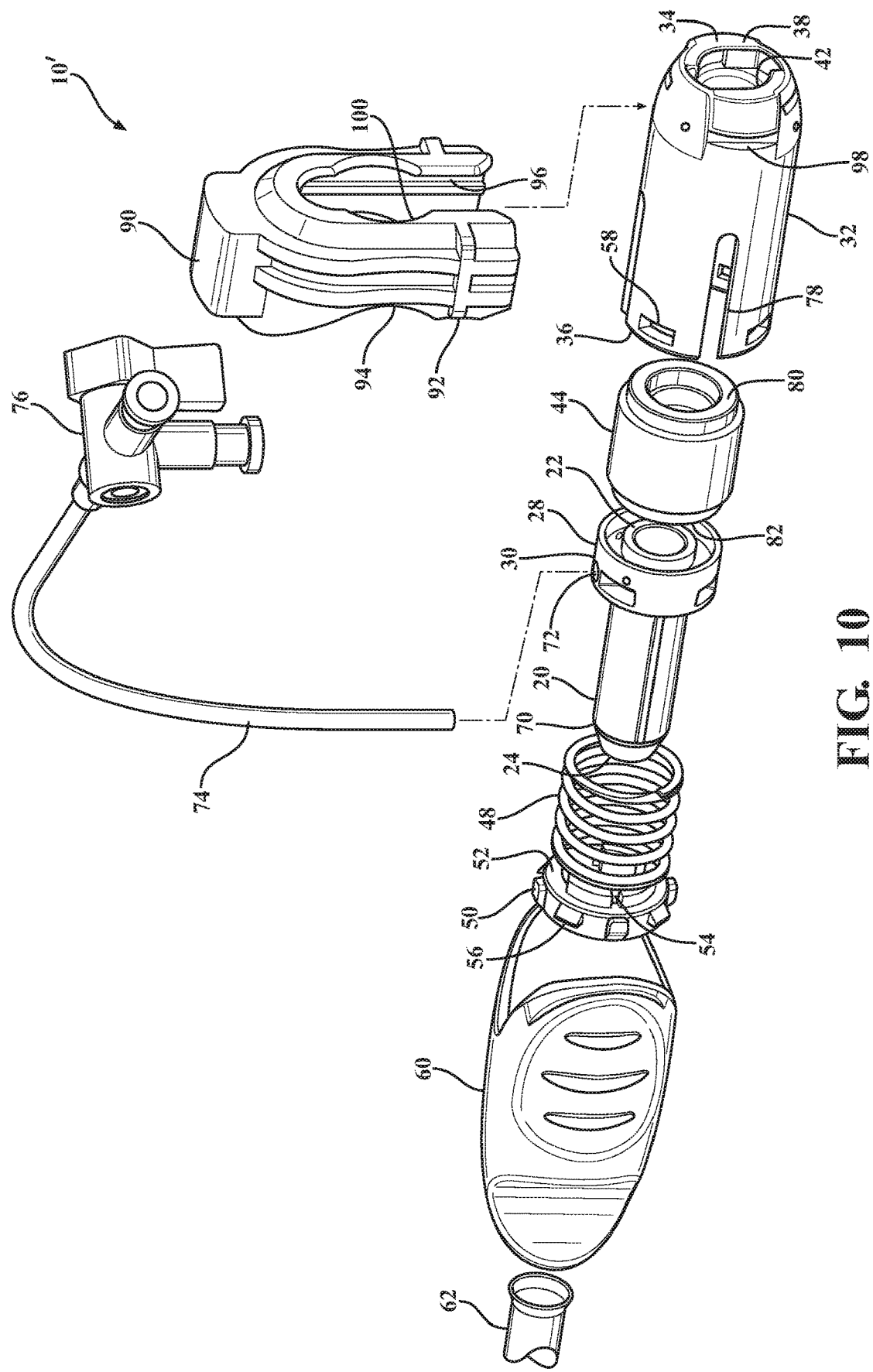
FIG. 10 is an exploded perspective view of the second embodiment of the medical valve assembly.

In a preferred aspect, an end cap 50 is mechanically interconnected to the valve housing 32 at the distal valve housing end 36 and is disposed in surrounding relationship around the tube 20. The end cap 50 establishes a shoulder 52 extending radially inward from the valve housing 32 and which is disposed in engagement with the compression member 48. As best shown in FIGS. 2 and 10, the end cap 50 defines an end cap opening 54 disposed concentrically around the distal tube end 24 of the tube 30 for serving as a guide for the tube 20, keeping the tube 20 concentric to the valve housing 32 and the elastomeric seal 44. As best shown in FIGS. 2 and 10, in each embodiment of the medical valve assembly 10, 10', the end cap 50 includes a plurality of locking tabs 56 extending radially therefrom and the valve housing 32 defines a plurality of corresponding locking apertures 58 disposed circumferentially about the distal valve housing end 36 for establishing the mechanical interlocked relationship between the end cap 50 and the valve housing 32.

Figure 3:
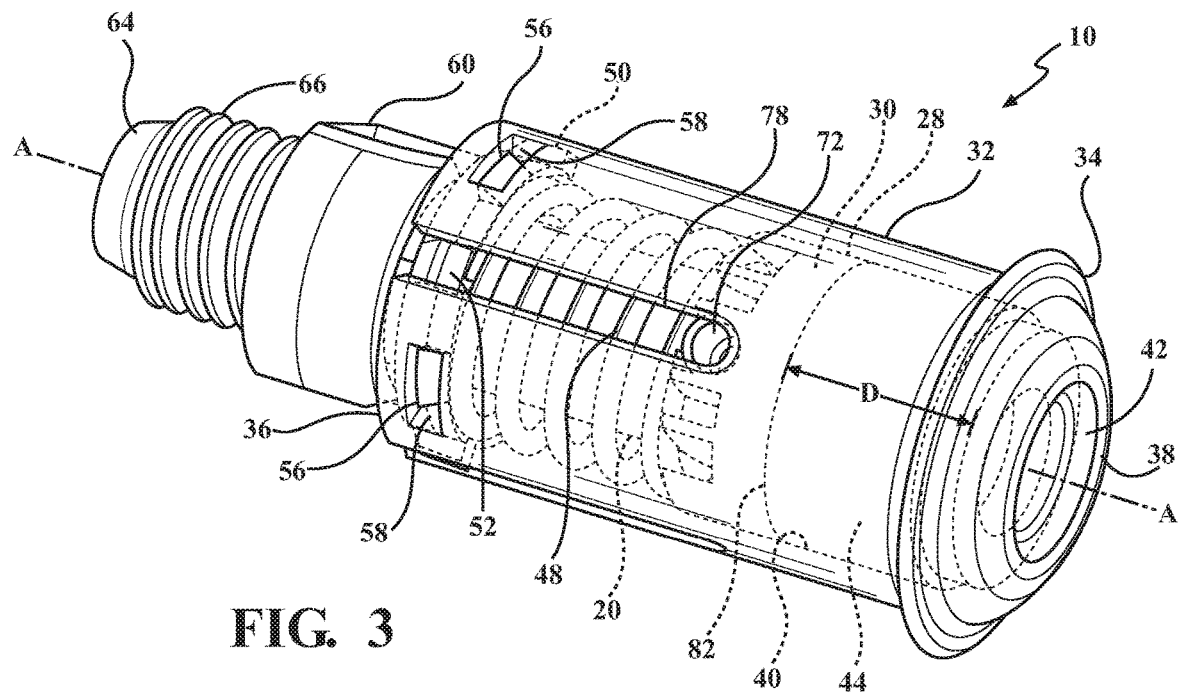
FIG. 3 is a perspective view of the first embodiment of the medical valve assembly.

As best shown in FIGS. 2, 3, 5, 10, and 14, a hub 60 is interconnected to the distal end 24 of the tube 20 for facilitating assembly of the medical valve assembly 10, 10' to an introducer sheath 62 or the like. As best shown in FIGS. 2 and 3, the hub 60 has a tapered portion 64 disposed adjacent a distal end of the medical valve assembly 10 for fitting the introducer sheath 64 over the tapered portion 64 of the hub 60. The hub 60 includes threads 66 disposed next adjacent the tapered portion 64 for allowing a compression nut 68 to be threadingly secured to the hub 60 for establishing a compression fit of the introducer sheath 62 between the compression nut 68 and the tapered portion 64 of the hub 60. As best shown in FIGS. 2 and 10, the tube 20 includes an o-ring 70 disposed about the distal tube end 24 to establish a sealed relationship between the tube 20 and the hub 60.

As best shown in FIGS. 2 and 10, the tube 20 defines an access hole 72 extending from the plunger plate surface 30 and radially through the plunger plate 28 to dispose the access hole 72 in fluid communication with the passageway 26. As best shown in FIGS. 1 and 9-13, the access hole 72 is connectable to an extension tube 74 and stop cock 76 for facilitating the flushing of the medical valve assembly 10 and/or the medical device 12 when inserted into the body vessel 14. As best shown in FIGS. 2, 3 and 10, the valve housing 32 can include at least one track 78 extending axially from the distal valve housing end 36 for receiving the extension tube 74 during attachment to the access hole 72. As the valve housing 32 or the tube 20 are axially moved relative to the other, the extension tube 74 is able to slide within the track 78 to prevent the extension tube 74 and stop cock 76 from being dislodged or accidentally removed from the access hole 72. If the medical application associated with the medical valve assembly 10, 10' does not require flushing or aspirating capabilities, the access hole 72 would preferably not be present or could alternatively be plugged.

Figure 6:
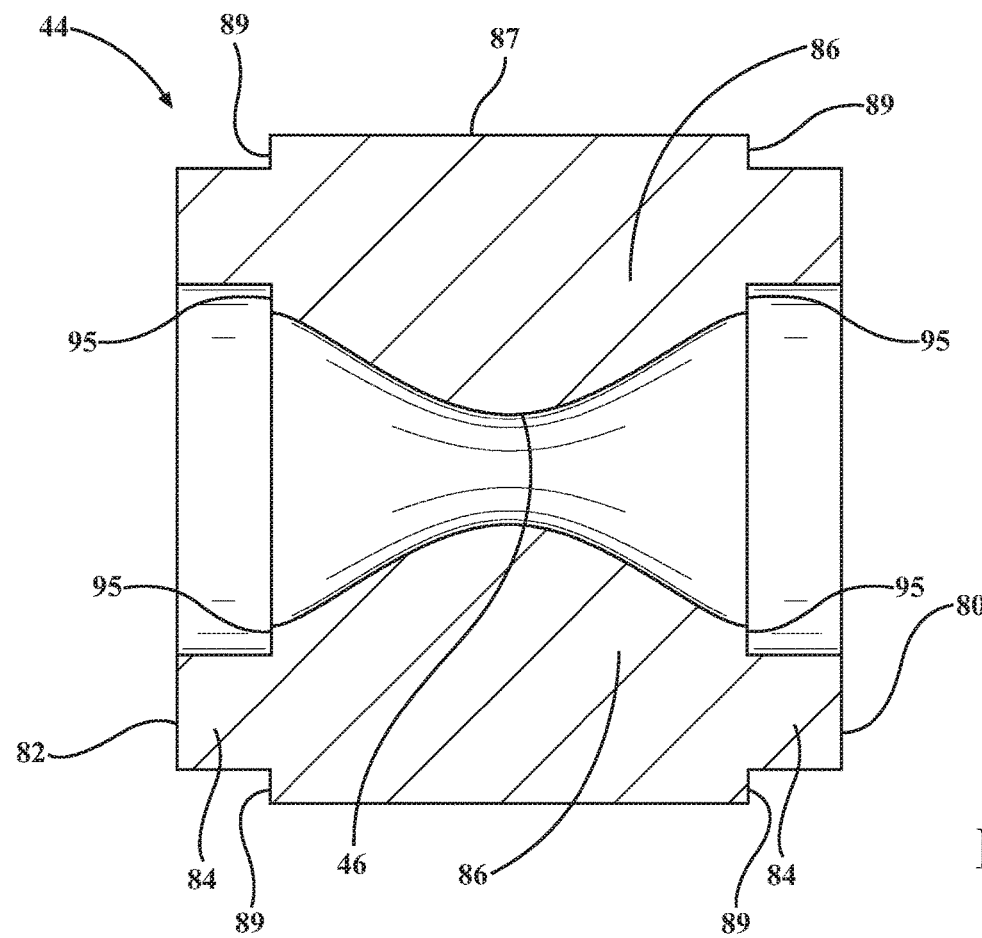
FIG. 6 is a cross-sectional view of an hour-glass shaped elastomeric seal.
Figure 7:
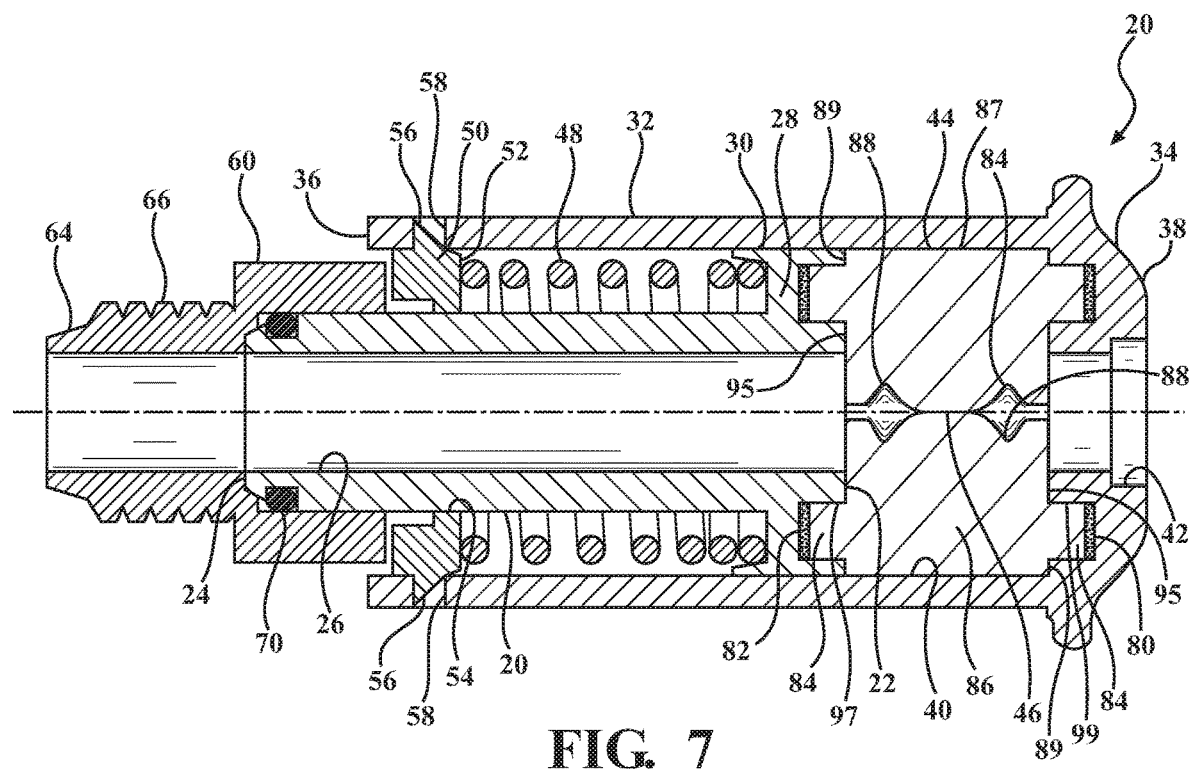
FIG. 7 is a cross-sectional view of the first embodiment of the medical valve including a slotted elastomeric seal disposed in a compressed or closed position.
Figure 16:
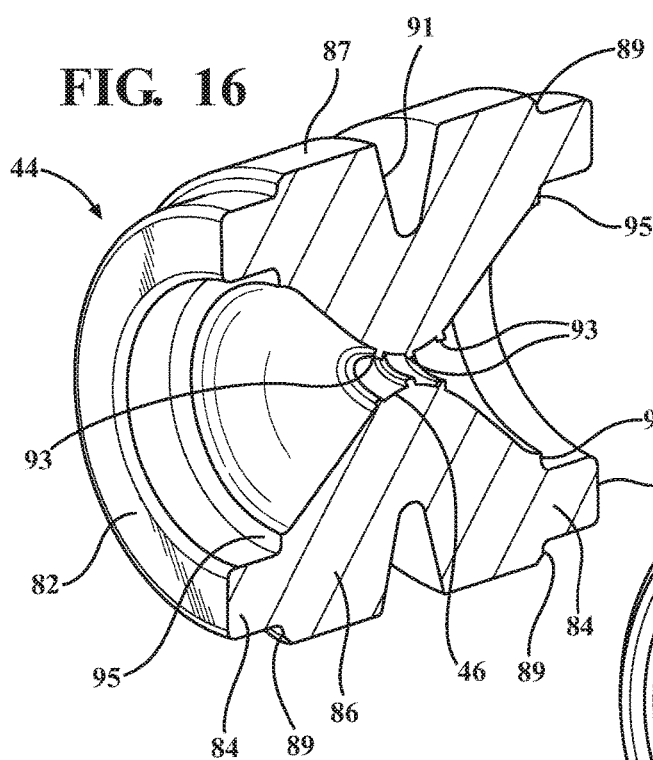
FIG. 16 is a perspective view of the alternative arrangement of the hour-glass shaped elastomeric seal.

As best shown in FIGS. 5, 6, 7, 14 and 16, the elastomeric seal 44 extends from a proximal seal end 80 to a distal seal end 82 to define a pair of end portions 84 disposed about a respective one of the seal ends 80, 82 and extending annularly around the axis A, each separated by a center portion 86. In each preferred embodiment of the medical valve assembly 10, 10', each of the annular end portions 84 are attached, secured or bonded respectively to the plunger plate 28 or the proximal valve housing end 34 of the valve housing 32 to prevent displacement of the elastomeric seal 44 and avoid the impingement of the elastomeric seal 34 between various medical devices 12, such as a lumen, catheter, or the like, entering or disposed within the medical valve assembly 10. As best shown in FIGS. 6 and 16, in an aspect, the center portion 86 of the elastomeric seal 44 is tapered radially inwards from the end portions 84 towards the inner diameter 46 disposed along a middle of the center portion 86 in a non-compressed state of the elastomeric seal 44 to define an hour-glass cross-sectional shape of the elastomeric seal 44, taken along a cross-sectional plane extending parallel with the axis A and between the proximal and distal seal ends 80, 82. As best shown in FIG. 7, according to another aspect, the inner diameter 46 extends circumferentially in parallel relationship with the axis A between the seal ends 80, 82 in a non-compressed state of the elastomeric seal 44. The elastomeric seal 44 defines a pair of slots 88 each extending radially inward from the inner diameter 46 and disposed between a respective end portion 84 and the center portion 86. In either aspect, the hour-glass cross-sectional shape or the slots 88 facilitate a compression of the elastomeric seal 44, allowing the center portion 86 to move radially inward during compression to establish the closed condition of the medical valve assembly 10.

Figure 15:
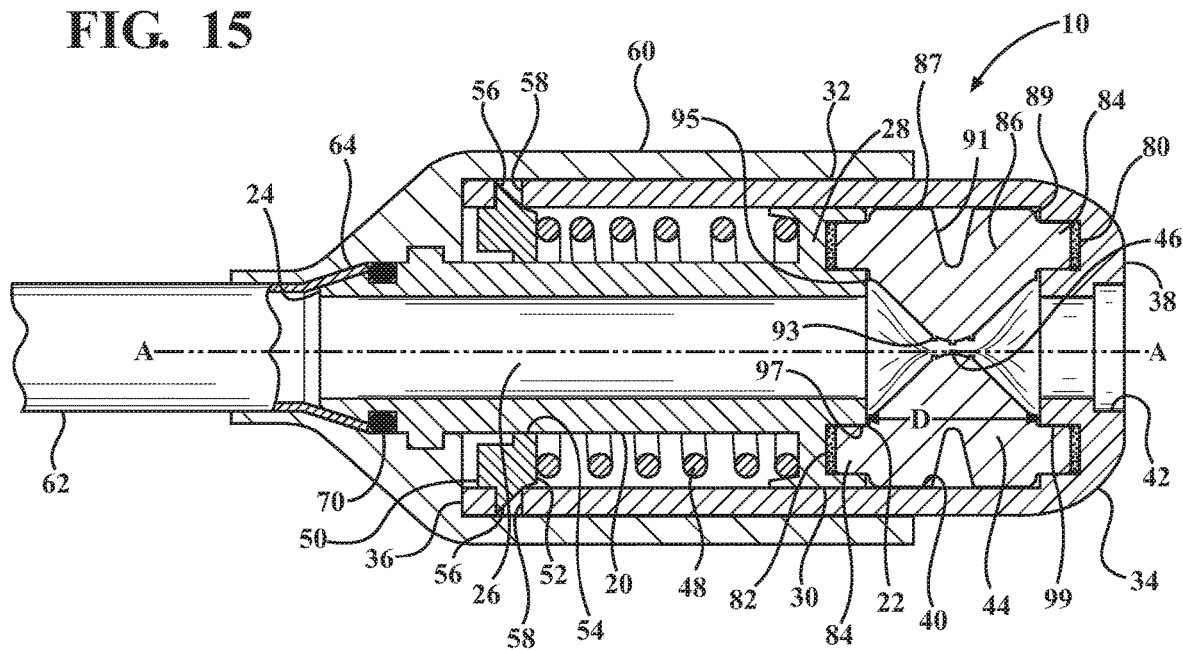
FIG. 15 is a cross-sectional view of the first embodiment of the medical valve assembly illustrating an alternative arrangement of the hour-glass shaped elastomeric seal.

As best shown in FIGS. 2, 6, 8, and 16, the center portion 86 of the elastomeric seal 44 includes an outer wall 87 disposed opposite the inner diameter 46 which extends radially outwardly past the end portions 84 to define a pair of outer annular shoulders 89 disposed adjacent the pair of end portions 84. As best shown in FIGS. 15 and 16, in an alternative and preferred arrangement of the hour-glass shaped elastomeric seal 44, the center portion 86 defines an annular void 91 extending radially inwardly from the outer wall 87 and towards the inner diameter 46 to remove or eliminate a portion of elastomeric material from the center portion 86 of the elastomeric seal 44. As such, the annular void 91 decreases the requisite compression force to effectuate a closing of the inner diameter 46 and allows the elastomeric seal 44 to be comprised of a elastomeric material having a higher or increased durometer value relative to an elastomeric seal 44 lacking the annular cavity 89—each of which ultimately improves the durability of the elastomeric seal 44. In a preferred arrangement, the annular void 91 has a wedge cross-sectional shape taken along a cross-sectional plane extending parallel to the axis A and between the proximal and distal seal ends 80, 82.

Figure 17:
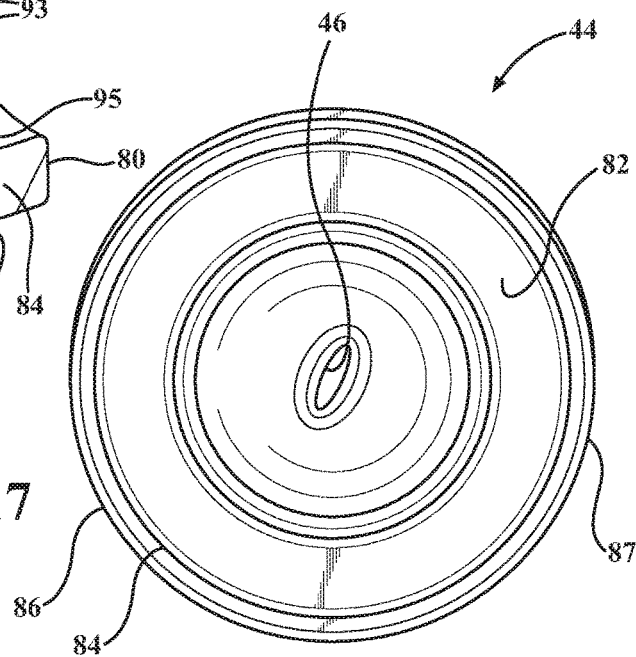
FIG. 17 is an end-view of the alternative arrangement of the hour-glass shaped elastomeric seal.

As best shown in FIGS. 15 and 16, the center portion 86 of the elastomeric seal 46 also includes a plurality of ribs 93 extending radially inwardly from the inner diameter 46 and encircling the axis A in concentric relationship with one another. As further illustrated in FIGS. 16 and 17, the inner diameter 46 of the elastomeric seal 44 is also preferably oval-shaped, as viewed from either seal end 80, 82, i.e., the oval cross-sectional shape of the inner diameter 46 is taken along a plane which extends perpendicular to the axis A and radially through the middle of the center portion 86 of the elastomeric seal 44. Each of the plurality of ribs 93 and the oval-shaped inner diameter 46 facilitate an improved closing of the inner diameter 46 in the compressed state of the elastomeric seal 44, i.e., the closed condition of the medical valve assembly 10.

Figure 8:
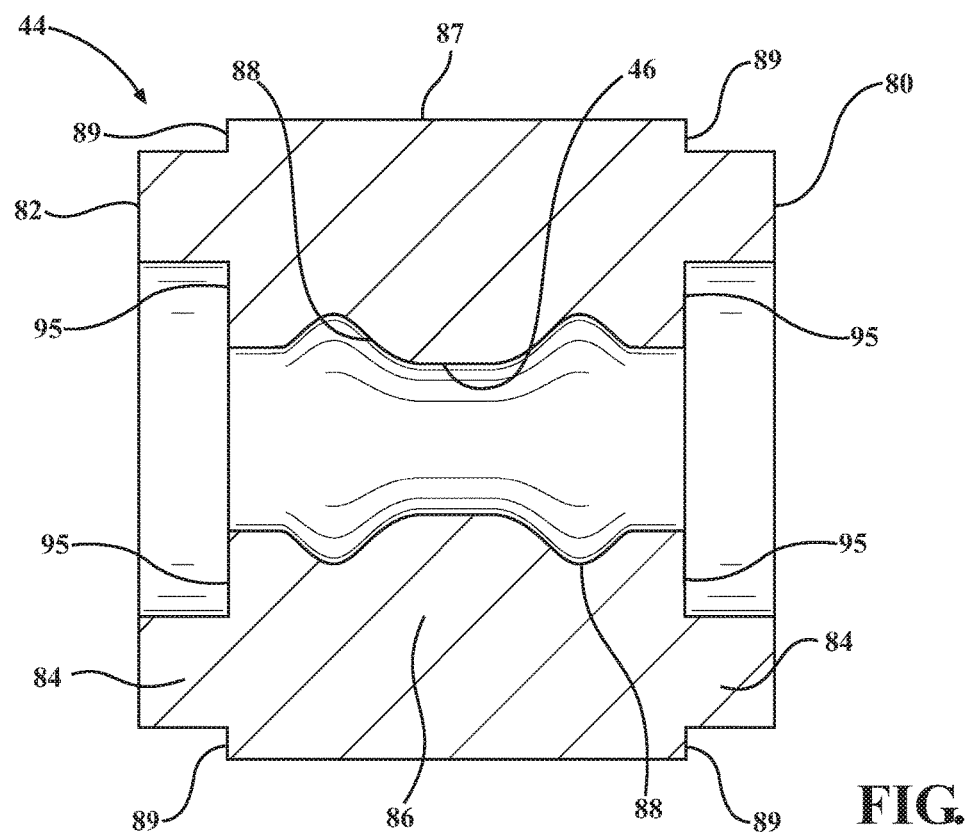
FIG. 8 is a cross-sectional view of the slotted elastomeric seal in an un-compressed condition.

As best illustrated in FIGS. 6, 8 and 16, the center portion 86 also extends radially inwardly adjacent the end portions 84 to define a pair of inner annular shoulders 95 disposed in opposing relationship to the pair of outer annular shoulders 89. In other words, the center portion 86 defines both the pair of outer annular shoulders 89 and the pair of inner annular shoulders 95 which are each disposed on opposite sides of the end portions 84. As best illustrated in FIGS. 2, 4-5, 7, 10 and 14-15, the plunger plate 28 defines a first annular channel 97 disposed adjacent the proximal tube end 22 and the flange 38 defines a second annular channel 99 disposed adjacent the proximal valve housing end 34. Each of the first and second annular channels 95, 97 extend annularly about the axis A and are open to the cavity 40. Accordingly, when the elastomeric seal 44 is installed in the cavity 40, the end portion 84 of the elastomeric seal 44 adjacent the distal seal end 82 is disposed within the first annular channel 95 to place the respective inner annular shoulder 95 in abutting relationship with the proximal tube end 22 and the outer annular shoulder 97 in abutting relationship with the plunger plate 28. Correspondingly, the end portion 84 of the elastomeric seal 44 adjacent the proximal seal end 84 is disposed within the second annular channel 97 to place the respective inner and outer annular shoulders 95, 97 in abutting relationship with the flange 38. Accordingly, the pair of inner and outer annular shoulders 95, 97 facilitates an improved compression of the elastomeric seal 44 between the plunger plate 28 and the flange 38. Additionally, as best illustrated in FIGS. 4-5, 7, and 14-15, the first and second annular channels 97, 99, which receive respective the end portions 84 of the elastomeric seal, allows the end portions 84 to more securely be attached, secured, or bonded respectively to the plunger plate 28 or the proximal valve housing end 34 of the valve housing 32 to further reduce the likelihood of displacement of the elastomeric seal 44.

As best shown in FIGS. 9-13, the second embodiment of the medical valve assembly 10' includes a clip 90 slidably and removably disposed over the proximal valve housing end 34 of the valve housing 32 for allowing a user of the medical valve assembly 10' to pre-open the elastomeric seal 44 prior to insertion of the medical device 12 into the medical valve assembly 10'. The pre-opening of the elastomeric seal 44 is advantageous when a medical device 12 for use with the medical valve assembly 10' is not sized or tapered at its insertion end to easily facilitate the initial automatic movement of the valve housing 32 and the tube 20 relative to the other to automatically open the medical valve assembly 10'. As will be described in more detail below, the clip 90 can also maintain the elastomeric seal 44 in a slightly opened position prior to use, such as when the medical valve assembly 10' is being stored or shipped, to increase the shelf life of the medical valve assembly 10' by reducing material creep, material sticking, or distortion of the elastomeric seal. Put another way, maintaining the elastomeric seal 44 in a slightly opened position keeps or reduces the mechanical load on various parts of the medical valve assembly 10'. Additionally, maintaining the medical valve assembly 10' in a slightly open position allows sterilization gases to pass through the elastomeric seal 44 and the tube 20 during a sterilization of the medical valve assembly 10'.

As best shown in FIGS. 10-13, in the second embodiment of the medical valve assembly 10', a proximal end of the hub 60 includes a curved or tapered profile and the clip 90 includes a first curved portion 92 and a second curved portion 94 each having a curvature profile that corresponds to the curved or tapered profile of the hub 60. The proximal valve housing end 34 defines a pair of guides 98 and the clip 90 includes a pair of rails 96 each disposed in mating and slidable relationship with a respective guide 98 when the clip 90 is disposed over the proximal valve housing end 34 of the valve housing 32.

Figure 11:
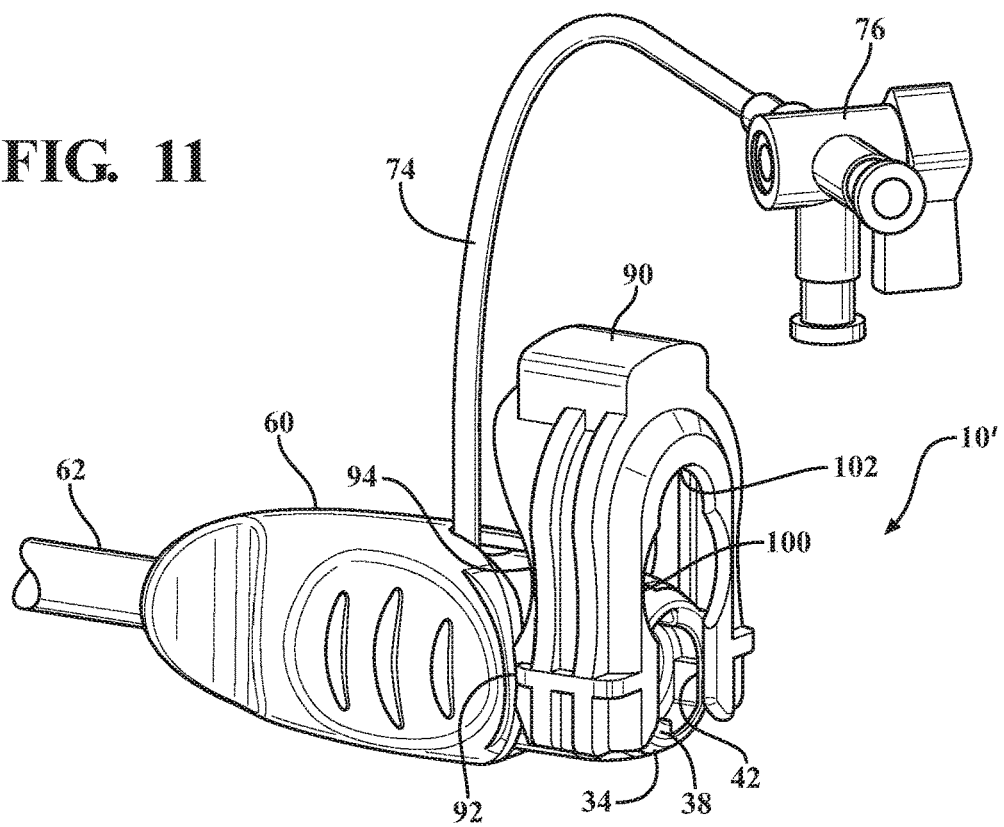
FIG. 11 is a perspective view of the second embodiment of the medical valve assembly illustrating a clip disposed in a first position.

As best shown in FIG. 11, when the clip 90 is initially disposed over the proximal valve housing end 34, the rails 96 mate and slide within the guides 98 to dispose the first curved portion 92 of the clip 90 in abutting and mating relationship with the curved profile of the hub 60 and define a first position of the clip 90. This first position effectuates a small axial movement of the valve housing 32 relative to the tube 20 for maintaining the elastomeric seal 44 in the slightly opened position. Put another way, when the clip 90 is disposed in the first position, a profile of the first curved portion 92 causes the pair of rails 96 to pull back on each of the respective guides 98, which axially pulls the valve housing 32 away from the tube 20 to allow the elastomeric seal 44 to axially expand and slightly increase the inner diameter of the elastomeric seal 44. As best shown in FIG. 11, since the first curved portion 92 of the clip 90 is sized to correspond to the curved profile of the hub 60, the clip 90 can remain in a fixed or stationary condition once placed in this first position until the clip 90 is removed by a user or advanced to the second position as described immediately below.

Figure 12:
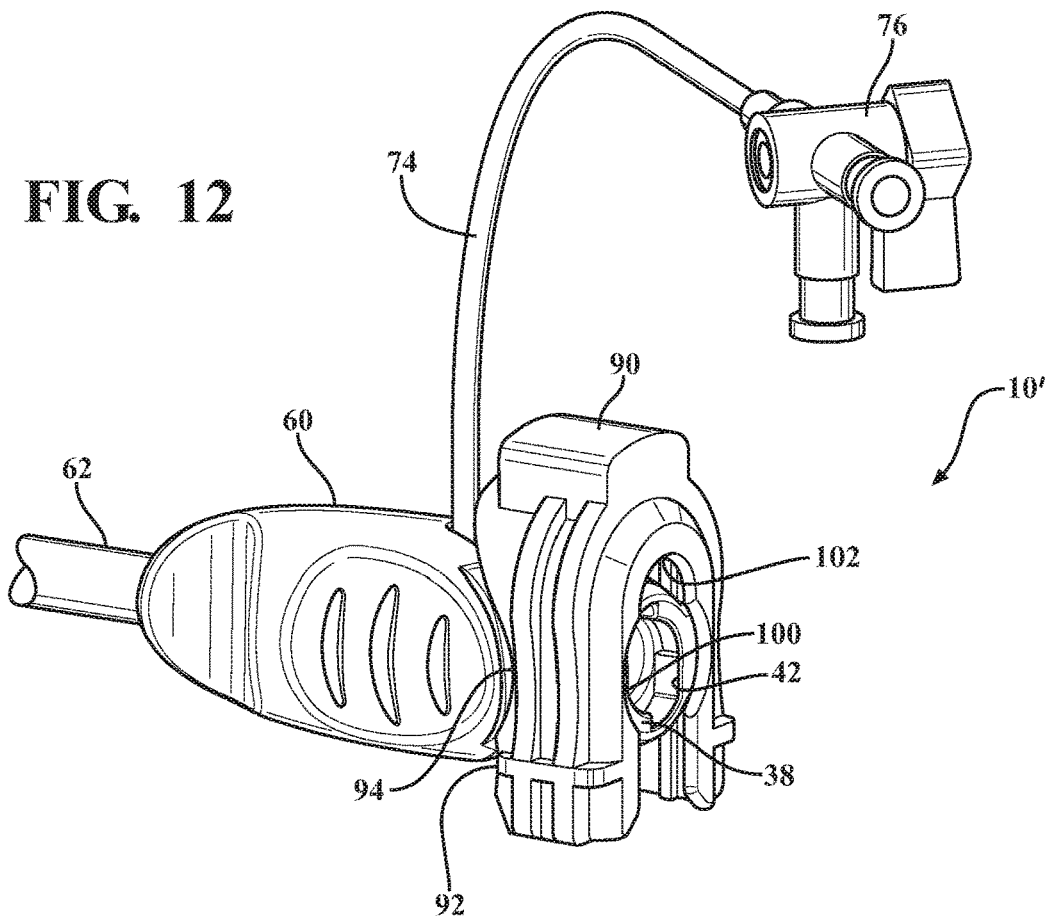
FIG. 12 is a perspective view of the second embodiment of the medical valve assembly illustrating the clip disposed in a second position.

As best shown in FIG. 12, a user of the medical valve assembly 10' can advance the clip 90 from its first position to dispose the second curved portion 94 in abutting and mating relationship with the curved profile of the hub 60 and define a second position of the clip 90. This second position returns the valve housing 32, and thus the elastomeric seal 44, back to their original and un-opened positions. Put another way, when the clip 90 is moved or advanced from the first position to the second position, a profile of the second curved portion 94 allows the pair of rails 96 to release their axial pull on each of the respective guides 98, which axially moves the valve housing 32 back towards the tube 20 and allows the compression member 48 to re-compress elastomeric seal 44 and re-close the medical valve assembly 10'. As best shown in FIG. 12, since the second curved portion 94 of the clip 90 is sized to correspond to the curved profile of the hub 60, the clip 90 can remain in a fixed or stationary condition in this second position until the clip 90 is returned to the first position or advanced to a third position, as will described immediately below. When the clip 90 is disposed in the second position, the clip 90 does not impact or affect the functionality of the medical valve assembly 10', allowing the medical valve assembly 10' to operate according to the aforementioned automatic principles. Accordingly, the clip 90 defines a clip opening 100 which is disposed in aligned relationship with the opening 42 of the valve housing 32 in the second position to allow the medical device 12 to be inserted serially through the clip opening 100, the opening 42, the inner diameter 46 of the elastomeric seal 44 and the passageway of the medical valve assembly 10'.

As best shown in FIG. 13, a user of the medical valve assembly 10' can advance the clip 90 from its second position to a third position by pushing on the clip 90 perpendicular to the axis A to slide the pair of guides 98 within each respective rail 96. The movement of the clip 90 slides the second curved portion 94 along the curved profile of the hub 60 to effectuate a manual axial movement of the valve housing 32 in the upward/proximal direction relative to the tube 20 for pre-opening the medical valve assembly 10'. Put another way, when the clip 90 is advanced from the second position towards the third position, the sliding movement of the hub 60 along the profile of the second curved portion 94 causes the pair of rails 96 to push upward/proximal on each of the respective guides 98 while radially sliding therein, which movement axially pulls the valve housing 32 away from the tube 20 to allow the elastomeric seal 44 to axially expand and increase the inner diameter of the elastomeric seal 44. As mentioned previously, this manual movement of the clip 90 from the second position to the third position allows a user of the medical valve assembly 10' to pre-open the elastomeric seal 44 prior to insertion of the medical device 12 into the medical valve assembly 10', such as when a medical device 12 being inserted into the medical valve assembly 10' is not sized or tapered to easily facilitate the initial automatic movement of the medical valve assembly 10'. As best shown in FIG. 13, the clip 90 additionally defines a slot 102 extending radially from the clip opening 100 and which is disposed in aligned relationship with the opening 42 of the valve housing 32 in the third position to allow the medical device 12 to be inserted serially through the slot 102, the opening 42 of the valve housing 36, the inner diameter 46 of the elastomeric seal 44 and the passageway of the medical valve assembly 10 while the clip is manually held in its third position. Once the medical device 12 is inserted into the medical valve assembly 10', a user can then release the manual pressure on the clip 90 which returns the clip 90 to the second position and allows the compression member 48 to compress the elastomeric seal 44 and automatically create a seal around the inserted medical device 12.

Although not expressly shown, a wiper seal can be disposed within the opening 42 of the valve housing 32. Additionally, in an aspect, the tube 20, valve housing 32, and end cap 50 are thermoplastic molded components and the elastomeric seal 44 is comprised of molded silicone. However, each of these components can be fabricated using other techniques or other elastomeric materials without departing from the scope of the subject disclosure.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A medical valve assembly for use in inserting a medical device into a body vessel of a patient, comprising:
    a tube having a proximal tube end and a distal tube end defining a passageway extending along an axis A between said tube ends;
    a plunger plate extending radially from said proximal tube end of said tube;
    a valve housing surrounding said tube about said proximal tube end and extending from a proximal valve housing end to a distal valve housing end;
    said valve housing including a flange extending radially inwards from said proximal valve housing end and disposed in spaced relationship with said plunger plate to define a distance dimension D extending therebetween;
    an elastomeric seal having an inner diameter, the elastomeric seal compressed between said plunger plate and said flange to reduce said inner diameter of said elastomeric seal and establish a closed condition of the medical valve assembly; and
    said elastomeric seal having an outer wall disposed in opposing relationship with said inner diameter and defining an annular cavity extending radially inwardly from said outer wall towards said inner diameter to decrease a requisite compression force for effectuating said reduction of said inner diameter of said elastomeric seal.

2. The medical valve assembly as set forth in claim 1, wherein said elastomeric seal extends between a proximal seal end disposed in abutting relationship with said flange and a distal seal end disposed in abutting relationship with said plunger plate, and said elastomeric seal being tapered radially inwards from next adjacent said end portions towards said inner diameter to define an hour-glass cross-sectional shape of said elastomeric seal in a non-compressed state.

3. The medical valve assembly as set forth in claim 2, wherein said elastomeric seal includes a plurality of ribs extending radially inwardly from said inner diameter and encircling said axis A in concentric relationship with one another.

4. The medical valve assembly as set forth in claim 3, wherein said inner diameter of said elastomeric seal being oval-shaped as viewed in cross-section.

5. The medical valve assembly as set forth in claim 2, wherein said elastomeric seal having a pair of end portions each disposed about a respective one of said seal ends and a center portion disposed between said end portions to define said outer wall, and said outer wall extending radially outwardly from said pair of end portions to define a pair of outer annular shoulders each respectively disposed in abutting relationship with one of said plunger plate or said flange.

6. The medical valve as set forth in claim 5, wherein said plunger plate defining a first annular channel disposed adjacent said proximal tube end, said flange defining a second annular channel disposed adjacent said proximal valve housing end, and each of said end portions extending annularly about said axis and respectively disposed within and secured to one of said first or second annular channels to prevent displacement of said elastomeric seal in said compressed state.

7. The medical valve assembly as set forth in claim 6, wherein said center portion extending radially inwardly adjacent said end portions to define a pair of inner annular shoulders respectively disposed in abutting relationship with one of said proximal tube end or said flange in said compressed state of said elastomeric valve.

8. The medical valve assembly as set forth in claim 1, wherein said annular void being wedge-shaped as viewed in cross-section.

9. The medical valve assembly as set forth in claim 4, wherein said elastomeric seal is configured to axially move one of the valve housing and the tube relative to the other when a medical device is inserted into the medical valve assembly and disposed in engaged relationship with said elastomeric seal to automatically increase the distance dimension between said plunger plate and said flange for allowing said inner diameter of the elastomeric seal to increase and establish an open and sealed condition of the medical valve assembly with the inserted medical valve.

10. The medical valve assembly as set forth in claim 1, further comprising a compression member disposed within said valve housing and biased against said plunger plate for decreasing said inner diameter to establish a closed condition of the medical valve assembly.

11. The medical valve assembly as set forth in claim 10, wherein said elastomeric seal is configured to transfer an insertion force exerted on said elastomeric seal by the inserted medical device to said compression member to effectuate the axial movement of one of the valve housing and the tube relative to the other.

12. An elastomeric seal for use with a medical valve assembly, comprising:
   a seal body extending along an axis A between a proximal seal end and a distal seal end;
   said body having a pair of end portions each respectively disposed about one of said seal ends and a center portion extending therebetween;
   said center portion being tapered radially inwards from said end portions towards an inner diameter of said elastomeric seal to define an hour-glass cross-sectional shape of the elastomeric seal;
   said center portion having an outer wall disposed in opposing relationship with said inner diameter and defining an annular void extending radially inwardly from said outer wall towards said inner diameter; and
   said elastomeric seal including a plurality of ribs extending radially inwardly from said inner diameter and encircling said axis A in concentric relationship with one another.

13. An elastomeric seal as set forth in claim 12, wherein said inner diameter of said elastomeric seal being oval-shaped as viewed in cross-section.

14. An elastomeric seal as set forth in claim 12, wherein said outer wall extending radially outwardly from said pair of end portions to define a pair of outer annular shoulders.

15. An elastomeric seal as set forth in claim 12, wherein said center portion extending radially inwardly adjacent said end portions to define a pair of inner annular shoulders.

16. An elastomeric seal as set forth in claim 12, wherein said annular void being wedge-shaped as viewed in cross-section.

* * * * *